(12) United States Patent
Kelleher et al.

(10) Patent No.: US 7,765,068 B2
(45) Date of Patent: Jul. 27, 2010

(54) IDENTIFICATION AND CHARACTERIZATION OF PROTEIN FRAGMENTS

(75) Inventors: Neil L. Kelleher, Urbana, IL (US); Gregory K. Taylor, Seattle, WA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1211 days.

(21) Appl. No.: 11/048,125

(22) Filed: Jan. 31, 2005

(65) Prior Publication Data

US 2006/0172430 A1 Aug. 3, 2006

(51) Int. Cl.
*G06F 19/00* (2006.01)
*G01N 24/00* (2006.01)
*H01J 49/00* (2006.01)

(52) U.S. Cl. .................... 702/19; 436/173; 250/281

(58) Field of Classification Search .................. None
See application file for complete search history.

(56) References Cited

U.S. PATENT DOCUMENTS

| | | | |
|---|---|---|---|
| 6,017,693 | A | 1/2000 | Yates, III et al. |
| 6,379,971 | B1 | 4/2002 | Schneider et al. |
| 2005/0112590 | A1 | 5/2005 | Boom et al. |
| 2005/0196809 | A1 | 9/2005 | Kelleher |

OTHER PUBLICATIONS

Belov, M, et al., "Electrospray ionization-fourier transform ion cyclotrom mass spectrometry using ion preselection and external accumulation for ultrahigh sensitivity"., J. Am. Soc. Mass Spectrom., vol. 12, pp. 38-48, (2001).
Biemann, K., et al., "Amino Acid Sequencing of Proteins"., Acc. Chem. Res., vol. 27, No. 11, pp. 370-378, (1994).
Clauser, K.R., et al., "Role of accurate mass measurement (+/- 10ppm) in protein identification strategies employing MS or MS/MS and database searching"., Analytical Chemistry, vol. 71, No. 14, pp. 2871-2882, (1999).
Creasy, D.M., et al., "Error tolerant searching of uninterpreted tandem mass spectrometry data"., Proteomlcs, vol. 2, pp. 1426-1434, (2002).
Eng, J.K., et al., "An approach to correlate Tandem Mass spectral data of peptides with amino acid sequences in a protein database"., J. Am. Soc. Mass Spectrom., vol. 5, pp. 976-989, (1994).
Ficarro, S.B., et al., "Phosphoproteome analysis by mass spectrometry and its application to *Saccharomyces cerevisiae*"., Nature Biotechnology, vol. 20, pp. 301-305, (2002).
Forbes, A.J., et al., "Toward efficient analysis of >70 kDa proteins with 100% sequence coverage"., Proteomics, vol. 1, pp. 927-933, (2001).
Garavelli, J.S., "The RESID database of protein modifications: 2003 developments"., Nucleic Acids Research, vol. 31, No. 1, pp. 499-501, (2003).
Ge, Y., et al., "Top down characterization of larger proteins (45 kDa) by electron capture dissociation mass spectrometry"., J. Am. Chem. Soc., vol. 124, No. 4, pp. 672-678, (2002).

Ge, Y., et al., "Top down characterization of secreted proteins from mycobacterium tuberculosis by electron capture dissociation mass spectrometry"., J. Am. Soc. Mass Spectrom, vol. 14, pp. 253-261, (2003).
Goshe, M.B., et al., "Phosphoprotein isotope-coded affinity tag approach for isolating and quantitating phosphopeptides in proteome-wide analyses"., Analytical Chemistry, vol. 73, No. 11, pp. 2578-2586, (2001).
Johnson, J.R., et al., "Fourier-transform mass spectrometry for automated fragmentation and identification of 5-20 kDa proteins in mixtures"., Electrophoresis, vol. 23, pp. 3217-3223, (2002).
Kachman, M.T., et al., "A 2-D liquid separations/mass mapping method for interlysate comparison of ovarian cancers"., Analytical Chemistry, vol. 74, No. 8, pp. 1779-1791, (2002).
Kelleher, N.L, et al., "Top down versus bottom up protein characterization by tandem high-resolution mass spectrometry"., J. Am. Chem. Soc., vol. 121, No. 4, pp. 806-812, (1999).
Kelleher, N.L, et al., "Efficient sequence analysis of the six gene products (7-74 kDa) from the *Escherichia coli* thiamin biosynthetic operon by tandem high-resolution mass spectrometry," Protein Science, vol. 7, pp. 1796-1801, (1998).
Kelleher, N.L., et al., "Thiaminase I (42 kDa) heterogeneity, sequence refinement, and active site location from high-resolution tandem mass spectrometry"., J. Am. Soc. Mass Spectrom, vol. 6, pp. 981-984, (1995).
Lander, E.S., et al., "Initial sequencing and analysis of the human genome"., Nature, vol. 409, pp. 860-921, (2001).
Li, W., et al., "Identification of intact proteins in mixtures by alternated capillary liquid chromatography electrospray ionization and LC ESI infrared multiphoton dissociation fourier transform ion cyclotron resonance mass spectrometry"., Analytical Chemistry, vol. 71, No. 19, pp. 4397-4402, (1999).

(Continued)

*Primary Examiner*—Lori A Clow
(74) *Attorney, Agent, or Firm*—Evan Law Group LLC

(57) ABSTRACT

A method of preparing a first set of candidate fragments from a sample protein fragment and a protein sequence, comprises selecting a first candidate sequence comprising a terminal amino acid of the protein sequence; generating a further candidate sequence from each candidate sequence, except a last candidate sequence; and including any candidate sequences having a mass which is equal to the mass of the sample protein fragment within a third tolerance, in the first set of candidate fragments. The generating of the further candidate sequences from each candidate sequence is by adding a portion of the protein sequence farther away from the terminal amino acid than the candidate sequence, if a mass of the sample protein fragment is equal to or greater than the mass of the candidate sequence within a first tolerance, or deleting a portion of the candidate sequence from an end closest to the terminal amino acid, if the mass of the sample protein fragment is less than the mass of the candidate sequence within a second tolerance. The candidate sequences are subsequences of the protein sequence.

11 Claims, 4 Drawing Sheets

OTHER PUBLICATIONS

MacCoss, M.J., et al, "Probability-based validation of protein identifications using a modified SEQUEST algorithm"., Analytical Chemistry, vol. 74, No. 21, pp. 5593-5599, (2002).

MacCoss, M.J., et al., "Shotgun identification of protein modifications from protein complexes and lens tissue"., Proc. Natl. Acad. Sci. USA, vol. 99, No. 12, pp. 7900-7905, (2002).

Meng, F., et al., "Informatics and multiplexing of intact protein identification in bacteria and the archaea" Nature Biotechnology, vol. 19, pp. 952-957, (2001).

Meng, F., et al, "Processing complex mixtures of intact proteins for direct analysis by mass spectrometry"., Analytical Chemistry, vol. 74, No. 13, pp. 2923-2929, (2002).

Mortz, E., et al., "Sequence Tag Identification of Intact Proteins by Matching Tandem Mass Spectral Data against Sequence Data Bases"., Proceedings of the National Academy of Sciences of the USA, vol. 93, No. 16, pp. 8264-8267, (1996).

Oda, Y., et al., "Accurate quantitation of protein expression and site-specific phosphorylation"., Proceedings of the National Academy of Sciences of the USA, vol. 96, pp. 6591-6596, (1999).

Oda, Y., et al., "Enrichment analysis of phosphorylated proteins as a tool for probing the phosphoproteome"., Nature Biotechnology, vol. 19, pp. 379-382, (2001).

Perkins, D., et al., "Probability-based protein identification by searching sequence databases using mass spectrometry data"., Electrophoresis, vol. 20, pp. 3551-3567, (1999).

Pineda, F.J., et al., "Testing the significance of microorganism identification by mass spectrometry and proteome database search"., analytical Chemistry, vol. 72, No. 16, pp. 3739-3744, (2000).

Reid, G.E., et al., "Gas-phase concentration, purification, and identification of whole proteins from complex mixtures"., J. Am. Chem. Soc., vol. 124, No. 25, pp. 7353-7362, (2002).

Reid, G.E., et al., "Tandem mass spectrometry of ribonuclease A and B: N-linked glycosylation site analysis of whole protein ions"., Analytical Chemistry, vol. 74, No. 3, pp. 577-583, (2002).

Taylor, G.K., et al., "Web and database software for identification of intact proteins using top down mass spectrometry"., Analytical Chemistry, vol. 75, No. 16, pp. 4081-4086, (2003).

Wilkins, M.R., et al., "High-throughput mass spectrometric discovery of protein post-translational modifications"., J. Mol. Biology, vol. 289, pp. 645-657, (1999).

Zhang, W., et al., "ProFound: An expert system for protein identification using mass spectrometric peptide mapping information"., Analytical Chemistry, vol. 72, No. 11, pp. 2482-2489, (2000).

Mann, M., et al., "Error-tolerant identification of peptides in sequence databases by peptides in sequence tags"., Analytical Chemistry, vol. 66, No. 24, pp. 4390-4399, (1994).

Steen, H., et al., "Detection of tyrosine phosphorylated peptides by precursor ion scanning quadrupole TOF mass spectrometry in positive ion mode"., Analytical Chemistry, vol. 73, No. 7, pp. 1440-1448, (2001).

Masselon, C., et al., "Accurate mass multiplexed tandem mass spectrometry for high-throughput polypeptide identification from mixtures"., Analytical Chemistry, vol. 72, No. 8, pp. 1918-1924, (2000).

Zhou, H., et al., "A systematic approach to the analysis of protein phosphorylation"., Nature Biotechnology, vol. 19, pp. 375-378, (2001).

Brancia, F.L., "Meeting Review: the $50^{th}$ ASMS conference on mass spectrometry and allied topics"., Orlando, Florida, USA, Jun. 2-6, 2002, Comparative and Functional Genomics, vol. 3, pp. 455-458, (2002).

Gerber, S.A., et al., "Absolute quantification of proteins and phosphoproteins from cell lysates by tandem MS"., PNAS, vol. 100, No. 12, pp. 6940-6945, (2003).

Forbes, A.J., et al., "Targeted analysis and discovery of post-translational modifications in proteins from methanogenic archaea by top-down MS"., PNAS, vol. 101, No. 9, pp. 2678-2683, (2004).

LeDuc, R.D., et al., "ProSight PTM: an integrated environment for protein identification and characterization by top-down mass spectrometry"., Nucleic Acids Research, vol. 32, web server issue, pp. W340-W345, (2004).

Meng, F., et al., "Informatics and multiplexing of intact protein identification in bacteria and the archaea"., Nature Biotechnology, vol. 19, pp. 952-957, (2001).

Pesavento, J.J., et al., "Shotgun annotation of histone modifications: A new approach for streamlined characterization of proteins by top down mass spectrometry"., J. Am. Chem. Soc., vol. 126, No. 11, pp. 3386-3387, (2004).

B Ions: 6    Y Ions: 6

| Ion | Observed Mass (Da) | Theoretical Mass (Da) | Mass Error (Da) | Mass Error (PPM) |
|---|---|---|---|---|
| B11 | 1321.820 | 1321.819 | 0.001 | 0.5 |
| B13 | 1547.910 | 1547.915 | -0.005 | -3.1 |
| B15 | 1744.040 | 1744.036 | 0.004 | 2.4 |
| B17 | 1914.140 | 1914.141 | -0.001 | -0.7 |
| B19 | 2113.270 | 2113.273 | -0.003 | -1.7 |
| B21 | 2339.360 | 2339.369 | -0.009 | -3.8 |
| Y12 | 1376.670 | 1376.671 | -0.001 | -0.4 |
| Y14 | 1618.800 | 1618.797 | 0.003 | 1.7 |
| Y16 | 1893.960 | 1893.961 | -0.001 | -0.3 |
| Y18 | 2052.030 | 2052.030 | 0.000 | 0.2 |
| Y20 | 2238.090 | 2238.094 | -0.004 | -1.7 |
| Y22 | 2482.210 | 2482.215 | -0.005 | -2.0 |

B Ions: 10    Y Ions: 0

| Ion | Observed Mass (Da) | Theoretical Mass (Da) | Mass Error (Da) | Mass Error (PPM) |
|---|---|---|---|---|
| B29 | 3114.855 | 3114.902 | -0.047 | -15.2 |
| B35 | 3740.162 | 3740.184 | -0.022 | -5.8 |
| B55 | 5945.418 | 5945.463 | -0.044 | -7.5 |
| B79 | 8715.946 | 8716.123 | -0.176 | -20.2 |
| B80 | 8829.102 | 8829.207 | -0.105 | -11.9 |
| B87 | 9675.459 | 9675.630 | -0.171 | -17.7 |
| B88 | 9774.596 | 9774.699 | -0.102 | -10.4 |
| B90 | 9974.623 | 9974.778 | -0.156 | -15.6 |
| B91 | 10121.678 | 10121.847 | -0.168 | -16.6 |
| B95 | 10534.975 | 10535.110 | -0.136 | -12.9 |

B

B Ions: 2    Y Ions: 3

| Ion | Observed Mass (Da) | Theoretical Mass (Da) | Mass Error (Da) | Mass Error (PPM) |
|---|---|---|---|---|
| B78 | 8715.946 | 8716.149 | -0.203 | -23.3 |
| B89 | 9955.626 | 9955.726 | -0.100 | -10.1 |
| Y80 | 8715.946 | 8716.084 | -0.137 | -15.7 |
| Y81 | 8829.102 | 8829.168 | -0.066 | -7.5 |
| Y90 | 9975.582 | 9975.786 | -0.204 | -20.5 |

IDENTIFICATION AND CHARACTERIZATION OF PROTEIN FRAGMENTS

COPYRIGHT NOTICE

A portion of the disclosure of this patent document contains material which is subject to copyright protection. The copyright owner has no objection to the facsimile reproduction by anyone of the patent document or the patent disclosure, as it appears in the patent and trademark office patent file or records, but otherwise reserves all copyright rights whatsoever.

APPENDIX MATERIALS

The appendix contains duplicate copies of one compact disk that provides software and database files and a paper Appendix identifying the compact disk that lists the files including the name, file size, and creation date of each. The contents of the compact disk and the paper Appendix are hereby incorporated by reference.

BACKGROUND

To a significant extent, the structural characterization of proteins relies on determining the primary structure (amino acid sequence and covalent modifications) of proteins as they are expressed under native cellular conditions. Once a protein is translated from mRNA, the primary structure of the protein is often covalently modified through the action of enzymes. These modifications include the addition of a new moiety to the side chain of an amino acid residue, such as the addition of phosphate to a serine or proteolytic cleavage, such as removal of an initiator methionine or a signal sequence. Thus, the structural characterization of a protein includes both the linear organization of the amino acid sequence (as affected by alternative splicing and polymorphisms) and the presence of any modification that may arise within the sequence.

Mass spectrometry (MS) is an analytical technique that is used to identify unknown compounds, to quantify known compounds, and to ascertain the structure of molecules. A mass spectrometer is an instrument that measures the masses of ions that have been converted from individual molecules. This instrument measures the molecular mass indirectly, in terms of a particular mass-to-charge ratio of the ions. The charge on an ion is denoted by the fundamental unit of charge of an electron z, and the mass-to-charge ratio m/z is mass of the ion divided by its charge. For singly-charged ions, the m/z ratio is the mass of a particular ion in Da.

The sample, which may be a solid, liquid, or vapor, enters the vacuum chamber of the instrument through an inlet. Electrostatic and/or magnetic filters are used to sort the ions according to their respective m/z ratios, and the ions are focused on the detector. In the detector, the ion flux is converted to a proportional electrical current. The instrument then records the magnitude of these electrical signals as a function of m/z and converts this information into a mass spectrum.

Tandem mass spectrometry (MS/MS) is a specific type of MS in which mass measurements of an intact ion and its constituent fragments are made in a single step. Generally in MS/MS, the intact mass of a protein ion is measured and the ion is isolated. Next, the instrument bombards ions of a sample with high intensity photons, electrons or neutral gas, breaking bonds, resulting in the formation of fragment ions from the molecular ions of the intact molecule. Although both positive and negative ions are generated with MS, only one polarity of an ion is detected with a particular instrumental set-up. Formation of gas phase sample ions allows the sorting of individual ions according to mass and their detection.

The masses measured by MS/MS may be used to identify a protein assuming it is contained in a database. One identification algorithm, absolute mass searching, allows the unambiguous identification and at least partial characterization of a protein from a sequence database using the intact mass in combination with fragment ion masses. Identification is achieved by selecting all candidate sequences from an annotated database that are within a user specified tolerance of an observed average or monoisotopic intact mass.

Each candidate sequence is scored against the observed fragment ions. This process involves calculating all theoretical b/y or c/z• type fragment ion masses (average or monoisotopic) from each candidate sequence and counting the number of observed fragment ions that are within a user specified tolerance (absolute or part per million) of any theoretical fragment ion. The number of observed fragment ions and the number of observed fragment ions that correspond to theoretical fragment ions are used to calculate the probability that the identification is spurious. All calculated scores are multiplied by the number of candidate sequences considered to yield a probability-based expectation value. The candidate protein with the lowest expectation value (and thus the lowest probability of being a spurious identification) is then considered the most likely candidate protein.

Living organisms are constantly synthesizing and degrading proteins. The degradation products of proteins are often found in various fluids of the organism, such as blood, urine, spinal fluid, cerebral spinal fluid, joints, saliva and serum. Many disease states include the production of an increased amount of a protein, the production of a protein form not normally produced, or a decrease in production of a protein. It is therefore possible to correlate the presence of the degradation products of proteins, also referred to as protein fragments or biomarkers, with disease states.

Precisely identifying biomarkers by MS, and deducing from which proteins they originated, presents significant challenges. Biomarkers are usually present in relatively low concentrations, which results in a low signal to noise ratio for the peaks in MS spectrum. Furthermore, this low signal to noise ratio usually results in fewer clearly identifiable fragment ions.

SUMMARY

In one aspect, the present invention is a method of preparing a first set of candidate fragments from a sample protein fragment and a protein sequence, comprising selecting a first candidate sequence comprising a terminal amino acid of the protein sequence; generating a further candidate sequence from each candidate sequence, except a last candidate sequence; and including any candidate sequences having a mass which is equal to the mass of the sample protein fragment within a third tolerance, in the first set of candidate fragments. The generating of the further candidate sequences from each candidate sequence is by adding a portion of the protein sequence farther away from the terminal amino acid than the candidate sequence, if a mass of the sample protein fragment is equal to or greater than the mass of the candidate sequence within a first tolerance, or deleting a portion of the candidate sequence from an end closest to the terminal amino acid, if the mass of the sample protein fragment is less than the mass of the candidate sequence within a second tolerance. The candidate sequences are subsequences of the protein sequence.

In a second aspect, the present invention is a method of preparing a second set of candidate fragments from a sample protein fragment and a plurality of protein sequences, comprising preparing a plurality of first sets of candidate fragments, where each first set is prepared from the sample protein fragment and each protein sequence; and including the first sets of candidate fragments in the second set of candidate fragments.

In a third aspect, the present invention is a method of preparing a first set of candidate fragments from a sample protein fragment and a plurality of protein sequences, comprising including in the first set of candidate fragments subsequences of the protein sequences in the plurality of protein sequences, where the candidate fragments have a mass which is the same as a mass of the sample protein fragment within a tolerance; and scoring the candidate fragments, by comparing mass spectrometry fragment ion masses of the candidate fragments with mass spectrometry fragment ion masses of the sample protein fragment.

In a fourth aspect, the present invention is a computer program product, comprising a computer readable medium having computer readable program code for preparing a first set of candidate fragments from a sample protein fragment and a protein sequence. The preparing of the first set comprises selecting a first candidate sequence comprising a terminal amino acid of the protein sequence; generating a further candidate sequence from each candidate sequence, except a last candidate sequence; and including any candidate sequences having a mass which is equal to the mass of the sample protein fragment within a third tolerance, in the first set of candidate fragments. The generating of the further candidate sequences from each candidate sequence is by adding a portion of the protein sequence farther away from the terminal amino acid than the candidate sequence, if a mass of the sample protein fragment is equal to or greater than the mass of the candidate sequence within a first tolerance, or deleting a portion of the candidate sequence from an end closest to the terminal amino acid, if the mass of the sample protein fragment is less than the mass of the candidate sequence within a second tolerance. The candidate sequences are subsequences of the protein sequence.

In a fifth aspect, the present invention is a computer program product, comprising a computer readable medium having computer readable program code for preparing a second set of candidate fragments from a sample protein fragment and a plurality of protein sequences. The preparing of the second set of candidate fragments comprises selecting a first candidate sequence for each protein sequence comprising a terminal amino acid of said each protein sequence; generating a further candidate sequence from each candidate sequence, except a last candidate sequence of said each protein sequence; and including any candidate sequences having a mass which is equal to the mass of the sample protein fragment within a third tolerance, in the second set of candidate fragments. The generating of the further candidate sequences from each candidate sequence is by adding a portion of said each protein sequence farther away from the terminal amino acid of said each protein sequence than the candidate sequence, if a mass of the sample protein fragment is equal to or greater than the mass of the candidate sequence within a first tolerance, or deleting a portion of the candidate sequence from an end closest to the terminal amino acid of said each protein sequence, if the mass of the sample protein fragment is less than the mass of the candidate sequence within a second tolerance. The candidate sequences are subsequences of said each protein sequence, each further candidate sequence comprises one more or one less amino acid than the candidate sequence from which the further candidate sequence was generated, and the first, second and third tolerances are equal.

In a sixth aspect, the present invention is a computer program product, comprising a computer readable medium having computer readable program code for preparing a first set of candidate fragments from a sample protein fragment and a plurality of protein sequences. The preparing the first set of candidate fragments comprises including in the first set of candidate fragments subsequences of the protein sequences in the plurality of protein sequences, where the candidate fragments have a mass which is the same as a mass of the sample protein fragment within a tolerance; and scoring the candidate fragments, by comparing mass spectrometry fragment ion masses of the candidate fragments with mass spectrometry fragment ion masses of the sample protein fragment.

Definitions

The term "fragment ions" is used when referring to fragments of a polypeptide generated by mass spectrometry.

The term "nascent polypeptide" refers to the initial translation product of a mRNA.

The term "modification," as used herein, refers to any chemical change in the primary structure of a nascent polypeptide. "Modification" of a protein includes: (i) a polymorphism at a codon position that results in a different amino acid within the primary structure of the protein; (ii) alternative splicing or RNA editing of a mRNA transcript that results in a different primary structure of a protein upon translation of the spliced or edited mRNA; and (iii) a chemical modification of the protein following its translation that results in a change in the molecular mass of the protein. Chemical modifications include naturally-occurring post-translational modifications as they arise in cells (e.g., proteolytic cleavage, protein splicing, N-Met and signal sequence removal, ribosylation, phosphorylation, alkylation, hydroxylation, glycosylation, oxidation, reduction, myristoylation, biotinylation, ubiquination, iodination, nitrosylation, amination, sulfur addition, peptide ligation, cyclization, nucleotide addition, fatty acid addition, acylation, etc.) as well as modifications that occur from sources not endogenous to biological cells (e.g., environmental mutagens, chemical carcinogens, experimentally-induced artificial modifications, etc.).

Shotgun annotation expands a database to include protein forms containing the designated modifications, and all combinations of these modifications (Pesavento, 2004). Shotgun annotation includes any type of modification, as the term "modification" is used herein.

The phrase "dynamically modify" refers to creating a change to a software program or database during the performance of a search.

The phrase "dynamic shotgun annotation" refers to creating shotgun annotations to protein structures in a database during the performance of a search.

The term "peptide" as used herein refers to a compound made up of a single chain of D- or L-amino acids or a mixture of D- and L-amino acids joined by peptide bonds. Preferably, peptides contain at least two amino acid residues and are less than about 50 amino acids in length.

"Polypeptide" as used herein refers to a polymer of at least two amino acid residues and which contains one or more peptide bonds. "Polypeptide" encompasses peptides and proteins, regardless of whether the polypeptide has a well-defined conformation.

The term "protein" as used herein refers to a compound that is composed of linearly arranged amino acids linked by peptide bonds. Proteins, as opposed to peptides, preferably contain chains of 50 or more amino acids. Although proteins are referred to throughout in the text, it is generally understood that the invention is applicable to all polypeptides.

The phrase "protein form" refers to a single species of a polypeptide or protein, including any modification. Thus, a single gene may encode many protein forms, depending upon the structure of the gene, the structure of the transcribed mRNA(s), and the nature of any modification(s).

The phrase "RNA splicing" refers to the removal of at least one intervening sequence of RNA by phosphodiester bond cleavage of two non-contiguous phosphodiester bonds within a given RNA and the joining the flanking exon RNA sequences by phosphodiester bond ligation.

The phrase "RNA editing" refers to an alteration in the nucleotide composition of an RNA sequence wherein at least one nucleobase of the transcribed RNA is replaced by another nucleobase of a different hydrogen bonding specificity. The resultant edited RNA may encode for a polymorphism, an extended polypeptide sequence (e.g., by eliminating a stop codon or by introducing an initiator codon), or a truncated polypeptide sequence (e.g., by introducing a stop codon).

The phrase "RNA processing" refers to any reaction that results in covalent modification of an RNA sequence. "RNA processing" encompasses both RNA splicing and RNA editing.

"Structure" as used herein with regard to proteins refers to the primary amino acid sequence of a protein, including modifications. The term "structure" and the phrase "primary structure" have the same meaning as used herein.

The phrase "warehouse database" refers to a collection of one or more protein forms.

A protein fragment results from degradation within an organism, or by intentional use of a protease.

A fragment ion is produced in the gas phase by MS/MS.

The term "subsequence" means a single contiguous piece of a sequence, such as a protein sequence.

BRIEF DESCRIPTION OF THE DRAWINGS

FIGS. 3A and B show the output from the slider algorithm for retrieval of a peptide fragment from ubiquitin-conjugating enzyme E2 N (SEQ ID NO: 1).
FIGS. 4A and B show the output from the slider algorithm run performed on MS/MS data for a yeast peptide: (A) ten fragment ion masses match up to a peptide from 60S ribosomal protein L27; (B) five fragment ion masses match to a probable membrane protein, NCBI protein accession no. Q12697.

DETAILED DESCRIPTION

The present invention makes use of a new search mode methodology and software platforms to determine protein fragment structure and origin. This new search mode, referred to as a slider search mode, uses the mass of the protein fragment (also referred to as the biomarker) to define the size of a window. This window scans across the length of the sequences of known proteins to identify candidate sequences which may correspond with the biomarker, and collects these as a set of candidate fragments. Then, optionally, the theoretical fragment ion masses of these candidate fragments is compared to the actual fragment ion mass values of the biomarker, scoring each candidate fragment, to thereby identify the structure and origin of the biomarker.

The slider algorithm reduces the number of candidate sequences compared to the observed intact mass from $O(n^2)$ to $O(n)$, where n is the number of amino acids in the protein sequence. An algorithm that considers all possible candidate sequences, must consider $O(n^2)$. This is done for the ith starting reference by considering all n−(i−1) possible ending references. In contrast, the slider algorithm compares 2(n−1) candidate sequences masses with the observed intact mass, as one mass is computed for each reference movement and each reference is moved exactly (n−1) times.

Slider Search Mode Methodology

Figure 1:
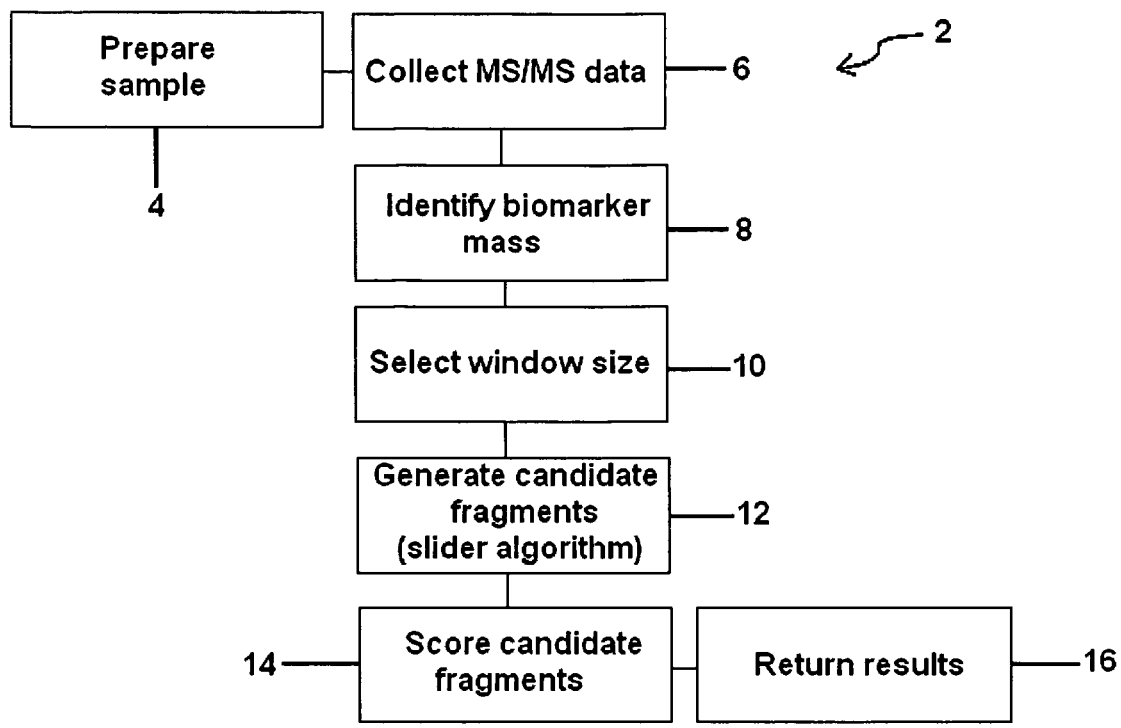
FIG. 1 is a flow chart of the slider search mode.

The slider search mode (2) is illustrated in FIG. 1. First, the sample is prepared for MS (4). Next, the MS/MS spectrum of the biomarker is collected (6). The intact mass of the biomarker is then identified (8). Optionally, the mass of the biomarker may be determined by methods other than MS. The intact mass of the biomarker, together with a chosen tolerance, is used to define a mass window size (10). Next, a slider algorithm generates a set 40 (shown in FIG. 2) of candidate fragments from a protein database (12). Then, optionally, the theoretical fragment ion masses of the candidate fragments are compared to the fragment ion mass values of the biomarker, to give each candidate fragment a score (14). Finally, the set of candidate fragments with its score is returned, or a subset of candidate fragments selected based on the scores is returned (16). The putative biomarker with the best score may identify the actual biomarker, and the protein from the database from which the putative biomarker originated may identify the protein from which the actual biomarker originated. The set of candidate fragments may include zero, one, or a plurality of candidate fragments.

Slider Algorithm

Figure 2:
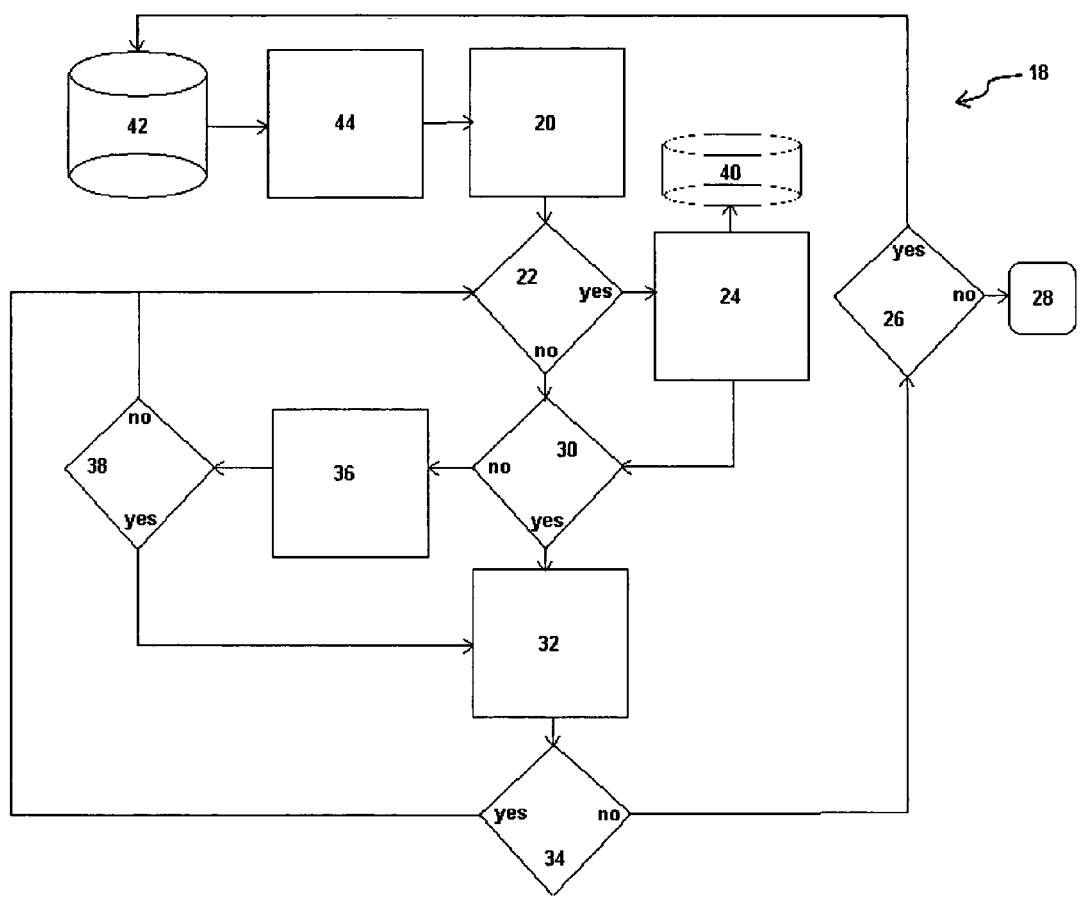
FIG. 2 is a flow chart of a slider algorithm.

A slider algorithm (18) flowchart is shown in FIG. 2. To start, a first protein sequence is selected from a protein database 42, and at an arbitrary terminus of the protein are set two references (a leading reference and a trailing reference) to the first amino acid in the protein (20). Optionally, the protein may be annotated or a set of annotated proteins may be generated (44). The references define a subsequence within the protein sequence. The subsequence defined by the two references is hence referred to as the candidate sequence. The leading reference signifies the candidate sequence beginning and the trailing reference signifies the candidate sequence end. At the start of the algorithm both references are at the starting terminus amino acid and define a candidate sequence containing one amino acid. Optionally, the references may be started at different amino acids, as long as one reference is set at a terminal amino acid.

Next, the mass window is compared to the mass of the candidate sequence (22). If the mass of the candidate sequence is the same as the mass window within a first user specified tolerance, then the candidate sequence is added to the set 40 of candidate fragments (24).

If the candidate sequence mass is less than or equal to the mass window within a second user specified tolerance (30), then the leading reference is set to a subsequent amino acid in the protein (32). If a subsequent amino acid does not exist (i.e. the leading reference is at the end of the candidate sequence) (34) then the algorithm continues at 26. Assuming that a subsequent amino acid exists, moving the references defines a new candidate sequence including one or more amino acid than the previous candidate sequence and the algorithm continues at 22. At 26 if there are more proteins sequences in the protein database (or annotated versions of the protein sequence) the algorithm begins again at 42, otherwise the algorithm terminates 28.

If the candidate sequence mass is greater than the mass window within a third user specified tolerance (30) the trailing reference is set to a subsequent amino acid (36). If the leading and trailing references are set at the same amino acid, (38), then the algorithm continues at 32, otherwise the references defines a new and smaller candidate sequence including at least one fewer amino acid than the previous candidate sequence and the algorithm continues at 22.

The references are moved to subsequent amino acids at 32 and 36. Preferably, the references are moved to the next subsequent amino acid, so that each candidate sequence contains one more or one less amino acid.

Scoring Candidate Fragments

One way to further analyze candidate fragments generated by a slider algorithm is to compare the theoretical fragment ion masses of the candidate fragments with the fragment ion masses of the biomarker (14). Each comparison is scored, and those candidate fragments that score above a threshold value are included in a set of putative biomarkers (16). The putative biomarker with the best score identifies the actual biomarker, and the protein from the database from which the putative biomarker originated identifies the protein from which the actual biomarker originated. Any scoring method may be used.

Mass Window Tolerance

The mass window size is based on the intact biomarker mass, which is identified from the MS/MS data. An absolute or relative tolerance is then selected, for example ±30 ppm or ±0.1 Da. A protein form is retrieved, and then the window moves along the length of the protein form to identify all possible candidate sequences within the protein form that have the same mass as that of the intact biomarker, and are within the selected tolerance. Three tolerances are selected, as noted above. Preferably, all three have the same value.

Warehouse Database of Protein Forms

The unannotated forms of proteins are available as FASTA files on publicly accessible databases throughout the world, such as SWISS-PROT, NCBI (National Center for Biotechnology Information) protein database, GenBank, and the like. These databases may be mined to enable one to create the desired warehouse database of protein forms tailored for the particular project at hand. Preferably, PERL scripts are used to convert FASTA files to the files that populate the warehouse database. While the FASTA file is converting, necessary information such as average and monoisotopic mass calculation and the number of amino acids in the sequence are added to the basic sequence from the FASTA file.

Shotgun Annotation of the Warehouse Database

Given that the absence in the database of the correct protein form from which the biomarker originated can hinder identification, a database warehouse of annotated sequences is created using the nomenclature of RESID, which is an authoritative database of known modification types (Garavelli, 2003). Having a database of protein forms allows one to consider known and putative modifications that may be indicated by the occurrence of distinctive sequence motifs.

Post-translational modification events that may be annotated in the databases include N-terminal acetylation, signal peptide prediction, phosphorylation, lipoylation, GPI anchoring, ribosylation, alkylation, hydroxylation, glycosylation, oxidation, reduction, myristylation, biotinylation, ubiquination, nitrosylation, amination, sulfur addition, peptide ligation, cyclization, nucleotide addition, fatty acid addition, acylation, proteolytic cleavage, etc. (about 150-200 post-translational modifications are known for polypeptides (Garavelli, 2003) and may be considered as annotations). One can obtain modification annotations from publicly available databases, such as SWISS-PROT, or by manually entering the modification annotations into the warehouse database.

Preferably, each warehouse database has three tables that incorporate gene attributes, protein form attributes, and modification attributes. The gene attributes include gene identification information and a detailed description of the structure of the gene. The protein form attributes include gene identification, protein form identification, monoisotopic mass, average mass, number of amino acids, and flags to any known attributes, such as a signal sequence, initiator methionine, etc. The modification attributes include modification (RESID) identification, average mass, monoisotopic mass, and RESID code attributes.

The main job of the warehouse database is to handle the queries from the window search algorithm. The database should return sequences quickly so as not to decrease the speed of the entire system. The table of protein forms contains most of the information that the window search algorithm needs. Since the table of protein forms already contains all the annotated sequences, one may obtain rapid responses from the database to queries from the window search algorithm.

Although sites of modification may be theoretically predicted from the genetic sequence of the protein, it is often not desirable to populate the annotation database with all potentially possible annotations. The inclusion of such annotations will yield unwieldy databases from the standpoints of their sheer size. Annotations should be selected based on the organism from which the sample originated, the specific fluid of the organism sampled, the condition of the sample, etc.

Once the window search algorithm selects a protein, then an expanded collection may be generated containing all possible annotations for those particular proteins. Therefore, a dynamic shotgun annotation of the warehouse database may be included in the window search approach.

Ion Predictor

The ion predictor predicts theoretical b/y and c/z ions, and is included in the software and system. Such calculations are useful for calculating errors, as expressed in terms of Daltons or parts-per-million.

Data Reduction Tool

A data reduction tool to remove redundant peaks resulting from multiple charge states and water/ammonia losses from reduced fragmentation data is included in the software and system. Such tools are useful for rapid analysis of the acquired MS data prior to its analysis by the retrieval algorithm.

Database Management System

Any database management system can be used with the warehouse database. Preferably, the database management system includes MySQL. This popular database system was selected because it has many useful supporting tools and APIs, and the system is readily available to the public. The software provided in the appendix uses version 11.18 distribution 3.23.52 MySQL for Linux.

Graphical Viewer Interface Tool

In all search methods, a collection of candidate protein fragments is returned with varying scores. A graphical viewer interface tool for viewing a collection of candidate protein fragments is included in the software and system. Optionally, the graphical viewer interface tool is incorporated into a local work station that includes the other features of the invention. Optionally, the graphical viewer interface tool is adapted for viewing data obtained via the internet from remote servers.

Databases Supported

The support databases can be configured for any organism. One embodiment supports databases for nine organisms, including: Saccharomyces cerevisiae, Escherichia coli, Arabidopsis thaliana, Bacillus subtilis, Methanococcus jannaschii, Mycoplasma pneumoniae, Shewanella oneidensis, Mus musculus and Homo sapiens. The yeast organism Saccharomyces cerevisiae database contains the most extensive annotations with known and predicted modification information.

Database Scalability

Of particular interest is how the database and search times scale with increasing modification information. A given gene and set of putative modifications results in an exponential number of protein forms where each form contains a subset of possible modifications. Thus, with n proteins and m possible processing events per protein, one embodiment includes a database containing $O(n2^m)$ protein forms. With a database of known and putative protein forms, an observed protein form may be identified and characterized, preferably with some modifications correctly predicted. An increase of spurious information in publicly accessible protein databases will render ambiguous some searches based upon sparse MS/MS data. However, the number of matching fragment ion masses will increase with more extensive and accurate modification information used during the query step.

Computer Interface With Mass Spectrometry Instrumentation

Optionally the components are organized on a computer system in communication with a mass spectrometer. In one embodiment, the computer is a local work station. In another embodiment, the computer is a server located off-site. In the latter embodiment, the components may be stored on the server and accessed using internet-based interface tools. The MS data generated from the mass spectrometer is transmitted to the computer for data acquisition and storage. The central processing unit of the computer coordinates analysis of the acquired MS data using the sliding window algorithm operating in one of the preferred embodiments to search the warehouse database of protein forms. Operator-specified tolerances are selected from options provided by the algorithm software to permit collection of protein candidates from the warehouse database of protein forms for further analysis of modifications.

Sample Preparation

Blood serum is one of the most common samples from which naturally occurring proteolytic products may be found. The slider algorithm allows identification of these peptides in their naturally occurring state, without further digestion by trypsin, etc.

To prepare a serum sample, the whole serum is first depleted of the highly abundant proteins that make up the vast majority of the protein matter in blood (e.g., albumin and IgG). This may be done either through commercially available affinity depletion protocols, or by ultrafiltration with a low molecular weight cut-off membrane (~50 kDa). The depleted serum is then fractionated by reversed phase liquid chromatography (RPLC) with either on-line or off-line electrospray ionization MS (ESI-MS). With an on-line liquid chromatography MS (LC-MS) (for example, using an LTQ-FT mass spectrometer, Thermo Electron Corp., Waltham, Mass.), fragmentation of detected species is accomplished on the fly using a normalized collision energy. The fragment ions are then analyzed using the Fourier transform analyzer in order to obtain isotopic resolution. For off-line RPLC followed by ESI-MS, a similar FTMS instrument is used to isolate and fragment each species in each fraction in an automated fashion.

The intact ion and fragment ion masses are then run through the slider algorithm for each species fragmented. The high mass accuracy afforded by FTMS instruments (typically <20 ppm) allows for highly specific and unambiguous identifications of each species.

Medical Applications

Some disease states are correlated with the presence of certain biomarkers. Other disease states are known to result in the production of proteins not normally produced. By identifying a biomarker which is a fragment of one of these proteins that is not normally produced, it may be concluded that the anomalous protein is being synthesized, and the presence of this protein may be correlated with the associated disease state.

Biomarker Discovery Algorithm: Software and Structure

The appendix contains a compact disk that provides all the necessary software tools and sample annotated warehouse database of protein forms to perform the disclosed aspects and embodiments. The system titled "Biomarker Discovery Algorithm" is a preferred embodiment.

Time-critical tasks, such as database retrieval and scoring, were written using an object-oriented design in C++ on Linux using the iODBC libraries for database connectivity. The data reduction tool is written in OCaml (chosen for language expressivity) while the visualization tool is written in PERL using the GD module for rendering images.

EXAMPLES

Example 1 (Prophetic Example)

The human protein NCBI protein accession no. P61089, Ubiquitin-conjugating enzyme E2 N, was chosen as a test case. A 61 amino acid peptide was chosen at random from this protein (RIIKETQRLLAEPVPGIKAEPDESNAR YFHVVIAGPQDSPFEGGTF KLELFLPEEYPMAAP)(SEQ ID NO:1), which has a theoretical mass of 6807.51 Daltons. Twelve theoretical b- and y-type fragment ion masses, and 12 other fragment ion masses that did not correspond to theoretical fragments, were included in the fragment ion mass list, entitled "UCEslider.pkl". This mass list was run through the slider algorithm, using a tolerance of ±30 ppm for both the intact and fragment ion masses. The data was run against the basic protein sequences in the NCBI protein database, and a minimum number of 5 fragment ion masses were required for a peptide to be retrieved.

FIGS. 3A and B show the output from the slider algorithm. FIG. 3A shows tabular results for the mass matches of the input fragment ion masses ("Observed Mass" column) vs. the calculated fragment ion masses ("Theoretical Mass" column). FIG. 3B is a graphical representation of the fragment ion mass matches for the retrieved peptide. The correct peptide was returned and all 12 theoretical fragment ion masses were matched to the peptide. None of the spurious fragment ion masses matched, and no other peptide was retrieved with 5 or greater fragment ion mass matches.

Example 2

The next example is of actual MS/MS data collected on a yeast proteolytic product from NCBI protein accession no. P38706, 60S ribosomal protein L27. The sample was generated by a multidimensional separation of a yeast whole cell lysate prior to Fourier transform MS (FTMS) analysis. Fragmentation via collisionally activated dissociation of the isolated intact species yielded 23 fragment ions. The masses of these ions, along with the intact mass of 10870.28 Da, were input into the slider algorithm and searched against the yeast protein database. Search parameters included a tolerance of ±40 ppm for the intact and fragment ion masses, the proper fragment type for the fragmentation method, and the minimum number of 5 fragment ion mass matches for a returned peptide.

The slider algorithm output returned two peptides with five or more fragment ion masses matching a mass list of 23 fragment ion masses. One peptide shows 10 of the 23 fragment ion masses matching, unambiguously identifying this peptide as belonging to 60S ribosomal protein L27 (NCBI protein accession no. P38706, peptide sequence: AKFLKAGKVAVVVRGRYAGKKVVIVKPHDEGS KSHPFGHALVAGIERYPLKVTKKHGAKKVAKRTKIK-PFIKVVNYNHLLPT RYTLDVEAFKSVVSTE) (SEQ ID NO:2). The results for this match are seen in FIG. 4A. FIG. 4B shows the next best match: a peptide with five fragment ion mass matches (from protein NCBI protein accession no. Q12697, a probable membrane protein; peptide sequence: HFHCDVRVLRDKFWTTISSSELVPGDIY EVSDPNITILPCDSILLSSDCIVNESMLTGES-VPVSKFPATEETMYQLCDDFQ STQISSFVSKSFLYNG) (SEQ ID NO:3). As shown in FIG. 4B, two of the five fragment ion masses matched are actually duplicates and should not be counted as real matches (B78/Y80 and B89/Y90).

REFERENCES

Belov M E, Nikolaev E N, Anderson G A, Auberry K J, Harkewicz R, Smith R D. "Electrospray-ionization-Fourier transform ion cyclotron mass spectrometry using ion preselection and external accumulation for ultrahigh sensitivity," *J. Am. Soc. Mass Spectrom.* 12:38-48 (2001).

Biemann K, Papayannopoulos I. *Acc. Chem. Res.* 27:370-78 (1994).

Clauser K R, Baker P, Burlingame A L. "Role of accurate mass measurement (+/−10 ppm) in protein identification strategies employing MS or MS/MS and database searching," *Anal. Chem.* 71:2871-82 (1999).

Ficarro S, McCleland M, Stukenberg P, Burke D, Ross M, Shabanowitz J, Hunt D, White F. "Phosphoproteome analysis by mass spectrometry and its application to *Saccharomyces cerevisiae*," *Nat. Biotechnol.* 20:301-305 (2002).

Garavelli, J S. "The RESID Database of Protein Modifications: 2003 developments," *Nucleic Acids Res.* 31:499-501 (2003).

Ge Y, Lawhorn B G, ElNaggar M Strauss E, Park J H, Begley T P, McLafferty F W. "Top down characterization of larger proteins (45 kDa) by electron capture dissociation mass spectrometry," *J. Am. Chem. Soc.* 124:672-78 (2002).

Ge Y, ElNaggar M, Sze S K, Bin O H, Begley T P, McLafferty F W, Boshoff H, Barry C E. *J. Am. Soc. Mass Spectrom.* 14:253-61 (2003).

Gerber S A, Rush J, Stemmann O, Steen H, Kirschner M W, Gygi S P. In: *50th ASMS Conference on Mass Spectrometry and Allied Topics*, Orlando, Fla., 2002.

Goshe M B, Conrads T P, Panisko E A, Angell N H, Veenstra T D, Smith R D. "Phosphoprotein isotope-coded affinity tag approach for isolating and quantitating phosphopeptides in proteome-wide analyses," *Anal. Chem.* 2001, 73:2578-86 (2001).

Johnson J R, Meng F, Forbes A J, Cargile B J, Kelleher N L. "Fourier-transform mass spectrometry for automated fragmentation and identification of 5-20 kDa proteins in mixtures," *Electrophoresis* 23:3217-23 (2002).

Kachman M T Wang H, Schwartz D R, Cho K R, Lubman D M. "A 2-D liquid separations/mass mapping method for interlysate comparison of ovarian cancers," *Anal. Chem.* 74:1779-91 (2002).

Kelleher N L, Costello C A, Begley T P, McLafferty F W. *J. Am. Soc. Mass Spectrom.* 6:981-84 (1995).

Kelleher N L, Taylor S V, Grannis D, Kinsland C, Chiu H J, Begley T P, McLafferty F W. "Efficient sequence analysis of the six gene products (7-74 kDa) from the *Escherichia coli* thiamin biosynthetic operon by tandem high-resolution mass spectrometry," *Protein Sci.* 7:1796-1801 (1998).

Lander E S et al. "Initial sequencing and analysis of the human genome," *Nature* 409:860-921 (2001).

MacCoss M J McDonald W H, Saraf A, Sadygov R, Clark J M, Tasto J J, Gould K L, Wolters D, Washburn M, Weiss A Clark J I, Yates J R., III. "Shotgun identification of protein modifications from protein complexes and lens tissue," *Proc. Natl. Acad. Sci. U.S.A.* 99:7900-7905 (2002).

Meng F, Cargile B J, Miller L M, Forbes A J, Johnson J R, Kelleher N L. "Informatics and multiplexing of intact protein identification in bacteria and the archaea," *Nat. Biotechnol.* 19:952-57 (2001).

Meng F, Cargile B J, Patrie S M, Johnson J R, McLoughlin S M, Kelleher N L. "Processing complex mixtures of intact proteins for direct analysis by mass spectrometry," *Anal. Chem.* 74:2923-29 (2002).

Oda Y, Huang K, Cross F R, Cowburn D, Chait B J, "Accurate quantitation of protein expression and site-specific phosphorylation," *Proc. Natl. Acad. Sci. U.S.A.* 96:6591-96 (1999).

Oda Y, Nagasu T, Chait B T. "Enrichment analysis of phosphorylated proteins as a tool for probing the phosphoproteome," *Nat. Biotechnol.* 19:379-82 (2001).

Perkins D, Pappin D, Creasy D, Cottrell J. "Probability-based protein identification by searching sequence databases using mass spectrometry data," *Electrophoresis* 20:3551-67 (1999).

Pesavento J J, Kim Y-B, Taylor G K, Kelleher N L. "Shotgun Annotation of Histone Modifications: A New Approach for Streamlined Characterization of Proteins by Top Down Mass Spectrometry," *J. Am. Chem. Soc.* (Communication) 126(11):3386-3387 (2004).

Pineda F J, Lin J S, Fenselau C, Demirev P A. "Testing the significance of microorganism identification by mass spectrometry and proteome database search," *Anal. Chem.* 72:3739-44 (2000).

Reid G E, Shang H, Hogan J M, Lee G U, McLuckey S A. "Gas-phase concentration, purification, and identification of whole proteins from complex mixtures," *J. Am. Chem. Soc.* 124:7353-62 (2002).

Reid G E, Stephenson J L, McLuckey S A. "Tandem mass spectrometry of ribonuclease A and B: N-linked glycosylation site analysis of whole protein ions," *Anal. Chem.* 74:577-83 (2002).

Steen H, Kuster B, Fernandez M, Pandey A, Mann M. "Detection of tyrosine phosphorylated peptides by precursor ion scanning quadrupole TOF mass spectrometry in positive ion mode," *Anal. Chem.* 73:1440-48 (2001).

Taylor G K, Kim Y B, Forbes A J, Meng F, McCarthy R, Kelleher N L "Web and database software for identification of intact proteins using top down mass spectrometry," *Anal. Chem.* 75:4081-86 (2003).

Wilkins M R, Gasteiger E, Gooley A A, Herbert B R, Molloy M P, Binz P A, Ou K, Sanchez J C, Bairoch A, Williams K L, Hochstrasser D F. "High-throughput mass spectrometric discovery of protein post-translational modifications," *J. Mol. Biol.* 289:645-57 (1999).

Zhang W, Chait B. "ProFound: an expert system for protein identification using mass spectrometric peptide mapping information," *Anal. Chem.* 72:2482-89 (2000).

Zhou H, Watts J D, Aebersold R. "A systematic approach to the analysis of protein phosphorylation," *Nat. Biotechnol.* 19:375-78 (2001).

The invention claimed is:

1. A method of determining the structure and origin of a sample protein fragment, comprising:
   collecting an MS/MS spectrum of the sample protein fragment,
   identifying the mass of the sample protein fragment,
   preparing a first set of candidate fragments from the sample protein fragment and a protein sequence selected from a protein sequence database, comprising:
      selecting a first candidate sequence comprising a terminal amino acid of the protein sequence;
      generating a further candidate sequence from each candidate sequence, except a last candidate sequence, by:
         adding a portion of the protein sequence farther away from the terminal amino acid than the candidate sequence, if a mass of the sample protein fragment is equal to or greater than the mass of the candidate sequence within a first tolerance, or
         deleting a portion of the candidate sequence from an end closest to the terminal amino acid, if the mass of the sample protein fragment is less than the mass of the candidate sequence within a second tolerance
      including any candidate sequences having a mass which is equal to the mass of the sample protein fragment within a third tolerance, in the first set of candidate fragments; and
      saving the first set of candidate fragments in a memory;
   wherein the candidate sequences are subsequences of the protein sequence.

2. The method of claim 1, wherein
   each further candidate sequence comprises one more or one less amino acid than the candidate sequence from which the further candidate sequence was generated, and
   the first, second and third tolerances are equal.

3. The method of claim 1, wherein the protein sequence is annotated.

4. The method of claim 1, further comprising scoring the candidate sequences in the first set of candidate fragments, by comparing mass spectrometry fragment ion masses of the candidate sequences in the first set of candidate fragments, with mass spectrometry fragment ion masses of the sample protein fragment.

5. A method of determining the structure and origin of a sample protein fragment, comprising:
   collecting an MS/MS spectrum of the sample protein fragment,
   identifying the mass of the sample protein fragment,
   preparing a first set of candidate fragments from the sample protein fragment and a plurality of protein sequences selected from a protein sequence database, comprising:
      including in the first set of candidate fragments subsequences of the protein sequences in the plurality of protein sequences, wherein the candidate fragments have a mass which is the same as a mass of the sample protein fragment within a tolerance;
      scoring the candidate fragments, by comparing mass spectrometry fragment ion masses of the candidate fragments with mass spectrometry fragment ion masses of the sample protein fragment;
      selecting a subset of candidate fragments, wherein the candidate fragments are selected based on the score; and
      saving the subset in a memory.

6. The method of claim 5, wherein the sample protein fragment is the candidate fragment with the mass spectrometry fragment ion masses most similar to the mass spectrometry fragment ion masses of the sample protein fragment.

7. The method of claim 5, further comprising generating the plurality of protein sequences by shotgun annotation of a database comprising at least one unannotated protein sequence.

8. The method of claim 5, further comprising generating the plurality of protein sequences by dynamic shotgun annotation of a database comprising at least one unannotated protein sequence.

9. The method of claim 5, wherein the sample protein fragment is from a mammal.

10. The method of claim 5, wherein the sample protein fragment is from blood, urine, spinal fluid, cerebral spinal fluid, joints, saliva or serum.

11. The method of claim 5, wherein the sample protein fragment is from a human.

* * * * *

SEQUENCE LISTING

<160> NUMBER OF SEQ ID NOS: 3

<210> SEQ ID NO 1
<211> LENGTH: 61
<212> TYPE: PRT
<213> ORGANISM: Homo sapiens

<400> SEQUENCE: 1

Arg Ile Ile Lys Glu Thr Gln Arg Leu Leu Ala Glu Pro Val Pro Gly
 1               5                  10                  15

Ile Lys Ala Glu Pro Asp Glu Ser Asn Ala Arg Tyr Phe His Val Val
            20                  25                  30

Ile Ala Gly Pro Gln Asp Ser Pro Phe Glu Gly Gly Thr Phe Lys Leu
        35                  40                  45

Glu Leu Phe Leu Pro Glu Glu Tyr Pro Met Ala Ala Pro
    50                  55                  60

<210> SEQ ID NO 2
<211> LENGTH: 98
<212> TYPE: PRT
<213> ORGANISM: Saccharomyces cerevisiae

<400> SEQUENCE: 2

Ala Lys Phe Leu Lys Ala Gly Lys Val Ala Val Val Arg Gly Arg
 1               5                  10                  15

Tyr Ala Gly Lys Lys Val Val Ile Val Lys Pro His Asp Glu Gly Ser
            20                  25                  30

Lys Ser His Pro Phe Gly His Ala Leu Val Ala Gly Ile Glu Arg Tyr
        35                  40                  45

Pro Leu Lys Val Thr Lys Lys His Gly Ala Lys Lys Val Ala Lys Arg
    50                  55                  60

Thr Lys Ile Lys Pro Phe Ile Lys Val Val Asn Tyr Asn His Leu Leu
65                  70                  75                  80

Pro Thr Arg Tyr Thr Leu Asp Val Glu Ala Phe Lys Ser Val Val Ser
                85                  90                  95

Thr Glu

<210> SEQ ID NO 3
<211> LENGTH: 97
<212> TYPE: PRT
<213> ORGANISM: Saccharomyces cerevisiae

<400> SEQUENCE: 3

His Phe His Cys Asp Val Arg Val Leu Arg Asp Lys Phe Trp Thr Thr
 1               5                  10                  15

Ile Ser Ser Glu Leu Val Pro Gly Asp Ile Tyr Glu Val Ser Asp
            20                  25                  30

```
-continued

Pro Asn Ile Thr Ile Leu Pro Cys Asp Ser Ile Leu Leu Ser Ser Asp
        35                  40                  45

Cys Ile Val Asn Glu Ser Met Leu Thr Gly Glu Ser Val Pro Val Ser
     50                  55                  60

Lys Phe Pro Ala Thr Glu Glu Thr Met Tyr Gln Leu Cys Asp Asp Phe
 65                  70                  75                  80

Gln Ser Thr Gln Ile Ser Ser Phe Val Ser Lys Ser Phe Leu Tyr Asn
                 85                  90                  95

Gly
```